(12) United States Patent
Hogrel

(10) Patent No.: US 11,058,335 B2
(45) Date of Patent: Jul. 13, 2021

(54) DEVICE FOR MEASURING A FORCE

(71) Applicant: ASSOCIATION INSTITUT DE MYOLOGIE, Paris (FR)

(72) Inventor: Jean-Yves Hogrel, Montrouge (FR)

(73) Assignee: ASSOCIATION INSTITUT DE MYOLOGIE, Paris (FR)

( * ) Notice: Subject to any disclaimer, the term of this patent is extended or adjusted under 35 U.S.C. 154(b) by 0 days.

(21) Appl. No.: 15/999,474

(22) PCT Filed: Feb. 15, 2017

(86) PCT No.: PCT/EP2017/053428
§ 371 (c)(1),
(2) Date: Aug. 17, 2018

(87) PCT Pub. No.: WO2017/140738
PCT Pub. Date: Aug. 24, 2017

(65) Prior Publication Data
US 2019/0226928 A1 Jul. 25, 2019

(30) Foreign Application Priority Data

Feb. 19, 2016 (FR) ..................................... 1651395

(51) Int. Cl.
*A61B 5/22* (2006.01)
*G01L 5/00* (2006.01)
*A61B 5/11* (2006.01)

(52) U.S. Cl.
CPC .............. *A61B 5/22* (2013.01); *A61B 5/1107* (2013.01); *A61B 5/224* (2013.01); *G01L 5/00* (2013.01)

(58) Field of Classification Search
CPC . G01L 5/16; G01L 5/00; A61B 5/1107; A61B 5/22; A61B 5/224; B63B 21/00
USPC ........................................................... 73/862
See application file for complete search history.

(56) References Cited

U.S. PATENT DOCUMENTS

| 3,680,368 A | 8/1972 | Warsaw |
| 4,501,148 A | 2/1985 | Nicholas et al. |
| 4,674,330 A * | 6/1987 | Ellis ........................ A61B 5/224 73/379.03 |
| 4,697,601 A * | 10/1987 | Durkee .................. A61B 5/228 600/590 |

(Continued)

FOREIGN PATENT DOCUMENTS

FR 2988838 A1 * 10/2013

OTHER PUBLICATIONS

French Search Report from French Patent Application No. 1651395, dated Oct. 5, 2016.

(Continued)

*Primary Examiner* — Octavia Hollington
(74) *Attorney, Agent, or Firm* — Greer, Burns & Crain, Ltd.

(57) ABSTRACT

A device for measuring a force, includes: a fastening apparatus; and a sensor, which includes a measuring member arranged to move along a measurement axis, the sensor being arranged to measure a force exerted on the measuring member depending on the movement of this measuring member. The fastening apparatus is arranged to exert, during a movement of the measuring member along this measurement axis, on a carrier to which they are fastened, an average force borne by the measurement axis.

9 Claims, 3 Drawing Sheets

(56) References Cited

U.S. PATENT DOCUMENTS

| | | | | |
|---|---|---|---|---|
| 5,095,764 | A * | 3/1992 | Saner | G01L 1/106 |
| | | | | 177/210 FP |
| 5,156,163 | A * | 10/1992 | Watkins | A61B 5/103 |
| | | | | 600/595 |
| 8,235,914 | B2 * | 8/2012 | Kojima | A61B 5/0006 |
| | | | | 600/573 |
| 9,267,779 | B2 * | 2/2016 | Emtman | G01B 3/205 |
| 9,782,624 | B2 * | 10/2017 | Braier | A63B 23/03508 |
| 9,888,966 | B2 * | 2/2018 | Farritor | B25J 9/1602 |
| 2012/0255355 | A1 * | 10/2012 | Xu | A61B 5/225 |
| | | | | 73/379.02 |
| 2013/0233323 | A1 * | 9/2013 | Koller-Hodac | A61H 1/008 |
| | | | | 128/845 |
| 2014/0371762 | A1 * | 12/2014 | Farritor | B25J 9/1633 |
| | | | | 606/130 |
| 2015/0047412 | A1 | 2/2015 | Hogrel | |

OTHER PUBLICATIONS

International Search Report from International Patent Application No. PCT/EP2017/053428, dated May 19, 2017.

Written Opinion of the International Searching Authority from International Patent Application No. PCT/EP2017/053428, dated May 19, 2017.

Mecmesin: "Myometer—Operator Manual", Nov. 1, 2014, retrieved from the Internet: <http://www.mecmesin.com/documents/manuals/431-378-03 Myometer.pdf>, retrieved Oct. 5, 2016.

* cited by examiner

DEVICE FOR MEASURING A FORCE

BACKGROUND

The present invention relates to a device for measuring a force.

The invention belongs to the field of metrology. The field of the invention is more particularly, but non-limitatively, that of measuring force on a patient who is potentially very weak, for example the extension or flexion force of a knee or the abduction of a shoulder or the flexion of an elbow.

Devices for measuring force on patients who are potentially very weak are known.

Among these devices, fixed dynamometry devices comprising a force sensor placed between two straps, one of which is fastened to a static fixed point (most often a point on a wall structure) and the other is attached to the patient by means of an ergonomic strap adjusted to the size of the patient and the size of the limb tested.

A technical problem posed by this type of device is that certain patients are so weak that they are not able to put the sensor and the strap under tension.

The purpose of the present invention is to solve this problem.

SUMMARY

This objective is achieved with a device for measuring a force comprising:
fastening means,
a sensor, comprising a measuring member arranged in order to be displaced along a measurement axis, said sensor being arranged in order to measure a force exerted on the measuring member as a function of the displacement of this measuring member,
characterized in that the fastening means are arranged so that, during a displacement of the measuring member along the measurement axis, they exert on
a support on which they are fastened an average force carried along the measurement axis.

The fastening means can comprise:
mechanical fastening means (jaws, clipping means, clamp band, etc.), preferably by clamping, comprising for example a vice comprising two jaws arranged in order to grip the support onto which the vice is attached, and/or
a suction cup and/or
a magnet.

The sensor preferably is accurate to 0.5 N or below.

The sensor preferably has a measuring range of at least 0 N to 900 N.

The device according to the invention can comprise an outer wall, the sensor being situated inside the outer wall so that the outer wall is equipped with a through hole facing the measuring member along the measurement axis. In this case:
the measuring member is preferably situated on a face of the sensor so that this face in not in contact with the outer wall, and/or
the measuring member can be equipped with a screw thread arranged in order to fasten to the measuring member an external element extending along the measurement axis through the through hole.

The device according to the invention can comprise at least one electronic board arranged for:
shaping an electronic signal originating from the sensor into force measurement data, and/or
supplying the sensor and/or other elements of the device with electricity, and/or
communicating, to outside the device, force measurement data originating from the sensor, and/or
storing force measurement data originating from the sensor.

The at least one electronic board extends preferably:
parallel to the measurement axis, and/or
under the sensor and under the fastening means.

According to yet another aspect of the invention, an assembly is proposed comprising:
a device according to the invention, in which the at least one electronic board is arranged for wireless communication, to outside the device, of force measurement data originating from the sensor, and
a remote means arranged in order to display the measurement data and/or to process the measurement data, said remote means being connected to said device by a wireless connection.

BRIEF DESCRIPTION OF THE DRAWINGS

Other advantages and features of the invention will become apparent on examination of the detailed description of implementations and embodiments which are in no way limitative, and the following attached drawings.

DETAILED DESCRIPTION

As these embodiments are in no way limitative, variants of the invention can be considered in particular comprising only a selection of the characteristics described or shown hereinafter, in isolation from the other characteristics described or shown (even if this selection is isolated within a sentence containing these other characteristics), if this selection of characteristics is sufficient to confer a technical advantage or to differentiate the invention with respect to the state of the prior art. This selection comprises at least one, preferably functional, characteristic without structural details, and/or with only a part of the structural details if this part alone is sufficient to confer a technical advantage or to differentiate the invention with respect to the state of the prior art.

Figure 1:
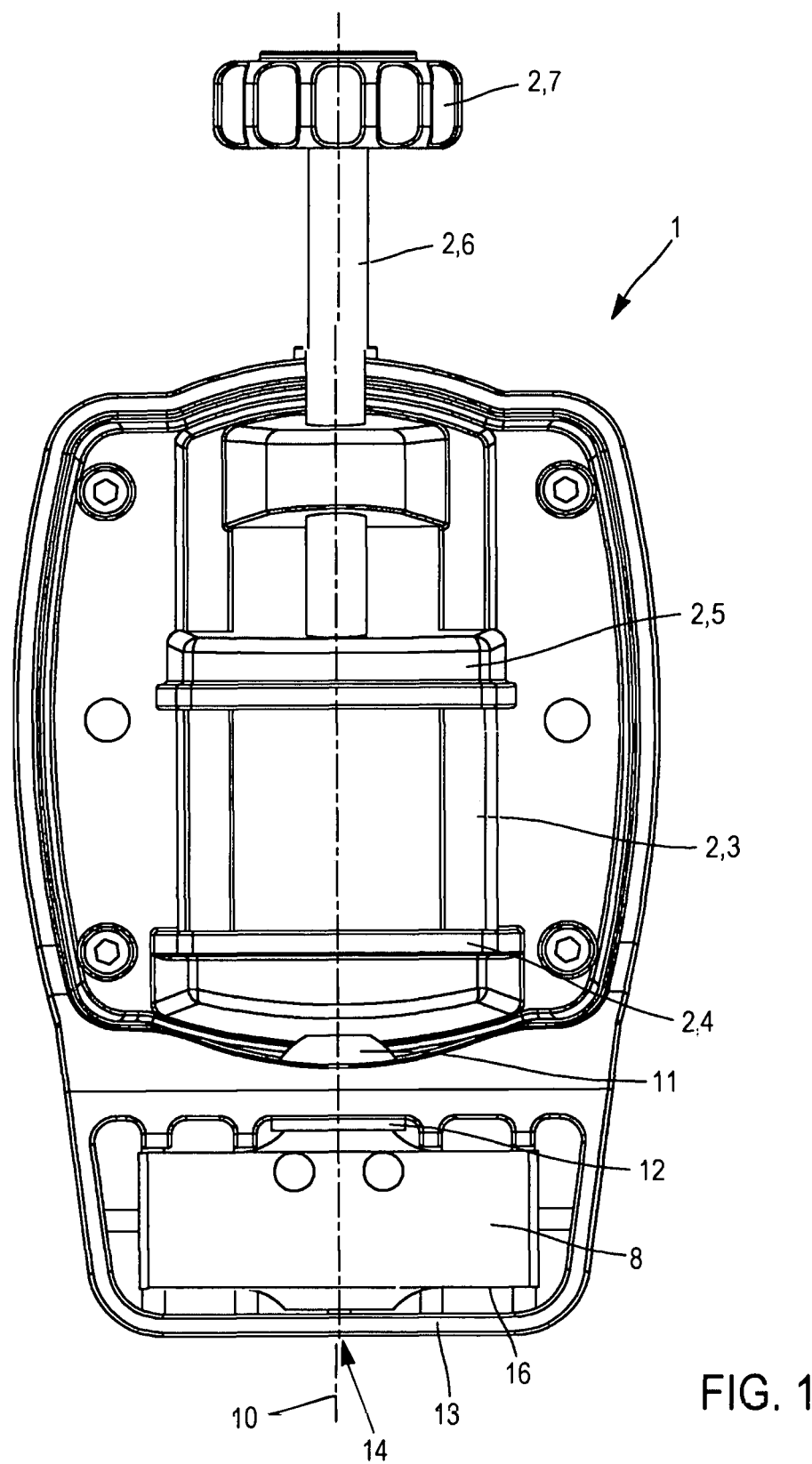
FIG. 1 is a top view of a first embodiment of the device according to the invention, which is the preferred embodiment of the invention.
Figure 2:
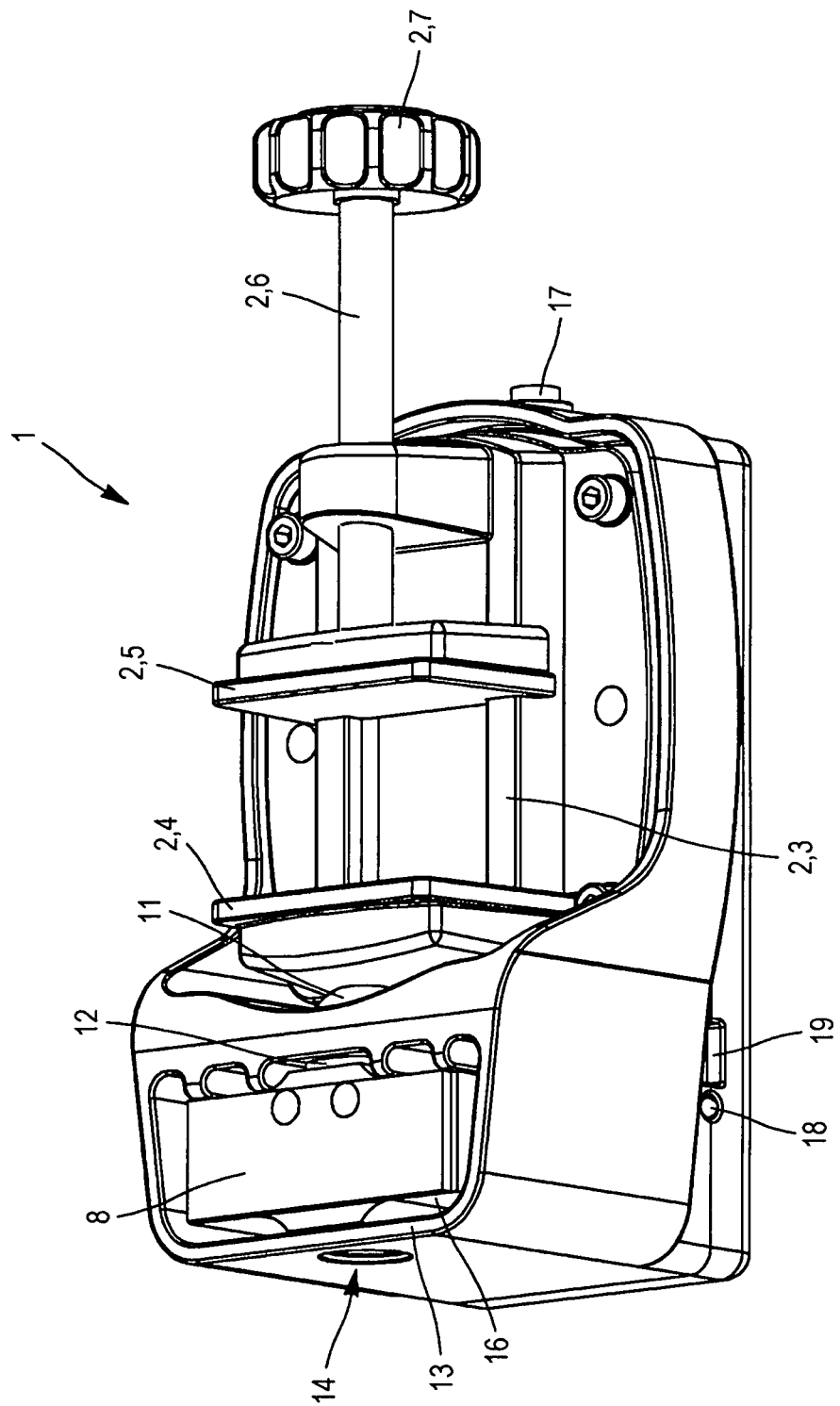
FIG. 2 is a perspective view of a side face of the first embodiment of the device according to the invention.
Figure 3:
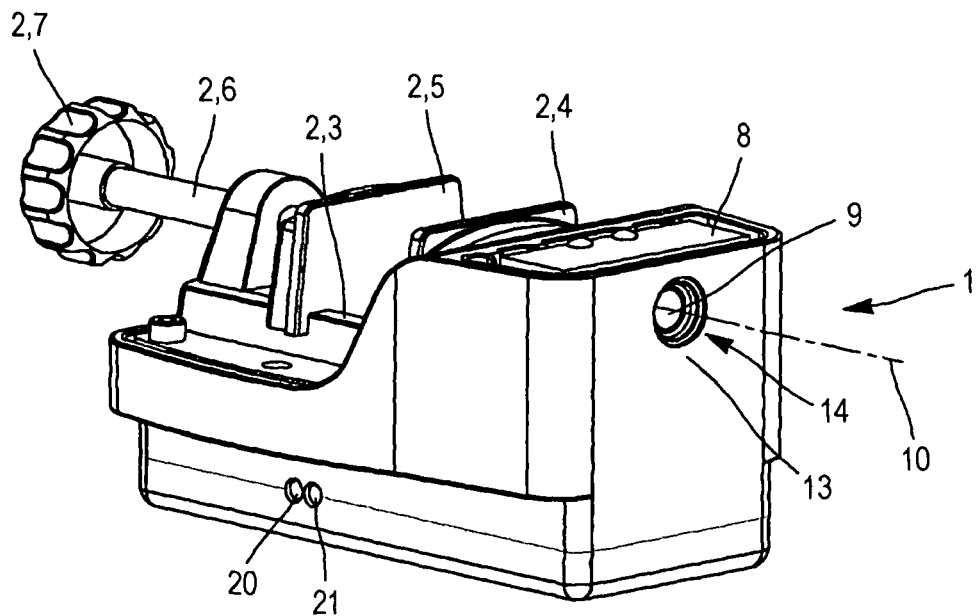
FIG. 3 is a perspective view of another side face of the first embodiment of the device according to the invention.
Figure 4:
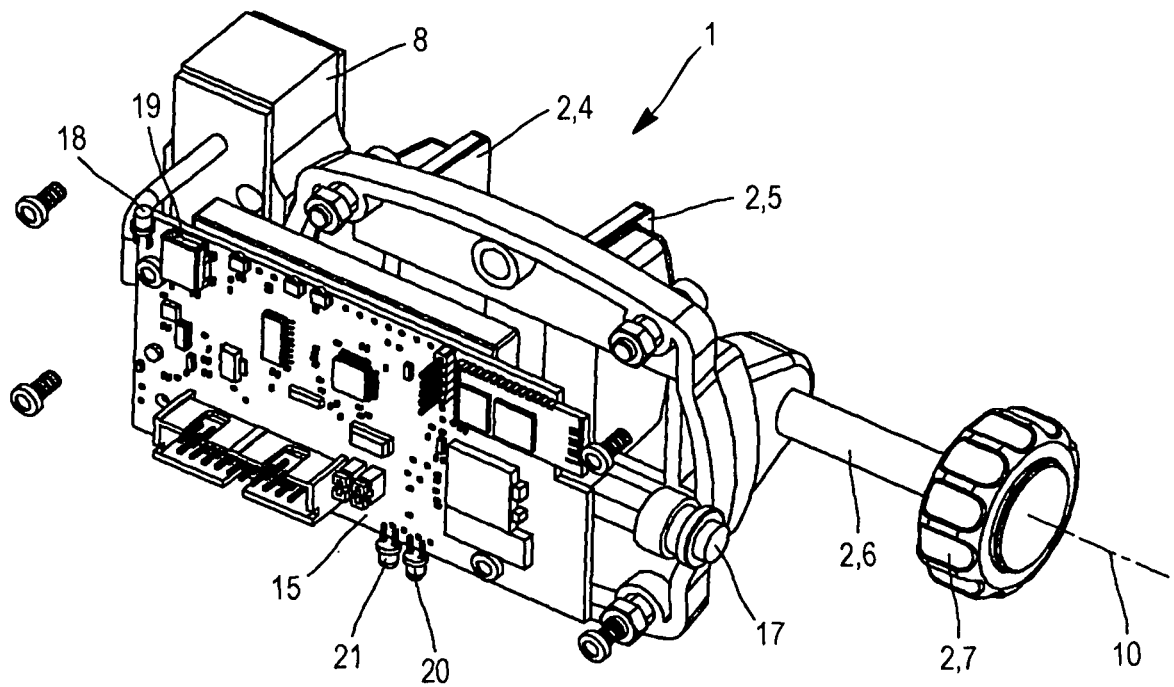
FIG. 4 is a perspective bottom view of the first embodiment of the device according to the invention, without its base plate in order to show the inside of the device according to the invention.

Firstly, with reference to FIGS. 1 to 4, a first embodiment of the device 1 according to the invention will be described.

The device 1 for measuring a force comprises:
fastening means 2, arranged in order to fasten the device 1 to a support, for example a bed, an ordinary table or a hospital table, a Bobath table, a chair, typically a leg or a frame or an edge of one of these elements,
a sensor 8, comprising a measuring member 9 (shown in FIG. 3) arranged in order to be displaced (with respect to the frame of the device 1) along a measurement axis 10 and only along this measurement axis 10, said sensor 8 being arranged in order to measure a force exerted on the measuring member 9 as a function of the displacement of this measuring member 9.

The fastening means 2 are arranged so that, during a displacement of the measuring member 9 along the measurement axis 10, they exert on a support on which they are fastened an average force carried along the measurement axis 10. In other words, the axis 10 of the sensor 8 is merged with the axis 10 of the fastening means 2.

An advantage of the invention is that the patient does not need to tense a strap in order to compensate for the weight of the sensor 8, which is particularly advantageous for weak patients having developed for example a neuromuscular, neurological or cardiovascular pathology and/or for elderly people.

The measuring member 9 of the sensor 8 is mobile with respect to the frame of the device 1. The sensor also comprises a housing that is static with respect to the frame of the device 1 and held fixed to the frame of the device 1 by fastening to the frame between a nut 11 and a washer 12.

The sensor 8 comprises a strain gauge or a dynamometer.

The sensor 8 used is an "SML Low Height Load Cell" sensor marketed by the company Interface Inc. for example with the reference SML-200 or SML-300. The preferred sensor 8 has a nominal capacity of approximately 89 kgf (200 lbf).

The sensor 8 can be calibrated by means of a method as described in patent FR 2 988 838.

The sensor 8 is accurate to 0.5 N or below and a resolution less than or equal to 0.1 N.

The sensor 8 has a measuring range reaching at least 900 N.

The device 1 is accompanied by a remote display means (not shown in the figures) arranged in order to display the measurement data and/or to process (change of scale, unit, reducing measurement noise, etc.) the measurement data, said remote means being connected to said device 1 by a wireless connection (for example by Bluetooth or Wifi).

This remote display means typically comprises a tablet (preferably touch-sensitive) or a PDA ("Personal Digital Assistant") or a smartphone or a wristband equipped with a screen (preferably touch-sensitive) and intended to be on the wrist of a person, typically on the wrist of the doctor or physiotherapist or any other medical personnel.

This remote means makes it possible to see the value for the force generated on the sensor 8 in real time, and to store the maximum value for each test.

This remote display means also comprises a battery (operating range of ten hours during a measurement by the sensor 8).

This remote display means also comprises means for storing the measurement data (typically at 50 Hz or 100 Hz) or for processing the measurement data.

This remote display means also comprises means (USB port or other) for exporting the measurement data or the processing of the measurement data to other technical means such as a computer.

This remote display means (for example a touch-sensitive tablet) is also a remote control means arranged in order to control certain functions of the device 1, in particular the calibration of the sensor 8 of the device 1.

The fastening means 2 comprise mechanical fastening means, typically means for fastening by clamping. The fastening means comprise a vice comprising:

two jaws 4, 5 arranged in order to grip the support on which the vice is attached, including one fixed jaw 4 with respect to the frame of the device 1 and one mobile jaw 5 with respect to the frame of the device 1, rails 3, arranged in order to guide a displacement of the mobile jaw 5 with respect to the frame of the device 1, a handle 7 and a rod 6, making it possible to displace the jaw 5 forwards or backwards parallel to the axis 10 according to the direction of rotation of the handle 7 and the rod 6.

The device 1 comprises an outer wall 13 (firmly fastened to the frame of the device 1). The sensor 8 is situated inside the outer wall 13 so that the outer wall 13 is equipped with a through hole 14 facing the measuring member 9 along the measurement axis 10, the measuring member 9 being situated on a face 16 of the sensor 8 so that this face 16 is not in contact with the outer wall 13. This makes it possible to ensure a better accuracy of measurement;

The measuring member 9 is equipped with a screw thread arranged in order to fasten to the measuring member 9 an external element extending along the measurement axis 10 through the through hole 14. This external element is typically a threaded rod firmly fastened to a hook or a loop or any other attachment system connected to a strap on which a user or a patient must pull or a rigid rod on which a user or patient must push.

The device 1 comprises at least one electronic board 15 arranged for:

shaping an electronic signal originating from the sensor 8 into force measurement data, supplying the sensor 8 and other elements of the device 1 with electricity, by means of a rechargeable battery having an operating range of ten hours during measurement by the sensor 8; the board 6 is arranged in order to control automatic shut-down of the device 1 and of the remote display means, after 10 minutes of non-use of the device 1 and of this remote means, communicating force measurement data originating from the sensor wirelessly (typically via Bluetooth or via a Wifi network) to outside the device (more precisely to the remote display means), storing force measurement data originating from the sensor 8, calibrating the sensor, typically controlled by the remote display and control means.

The at least one electronic board 15 extends parallel to the measurement axis 10, under the sensor 8 and under the fastening means 2.

In more detail, the at least one electronic board 15 comprises in particular sub-modules intended for the supply and electrical charging of the device 1, in particular a connector 19 (USB) for connecting to a source of electrical energy supply external to the device 1, a battery, a battery management sub-module, and a supply regulation sub-module for each element of the device 1 requiring a supply.

A diode 18 indicates, when it is switched on (typically green), a correct charge level of the battery of the device 1.

The at least one electronic board 15 also comprises a microcontroller.

The microcontroller advantageously comprises an EPROM (Erasable Programmable Read Only Memory).

The microcontroller can be connected to a computer and to the remote display means by means of a wireless connection (Bluetooth or Wifi) as well as by means of the connector 19. A diode 21 is switched on (typically red) when the wireless connection has failed or has a problem connecting with the remote display means.

The microcontroller module integrates several components and in particular a RAM, a FLASH memory and an analogue digital converter. These components are configured so as to allow calibration of the measurements of forces. To this end, a software programme is loaded in the memory of the microcontroller so as to carry out the calibration and the measurements of the sensor 8.

A button 17 makes it possible to switch the device 1 on and off. A diode 20 is illuminated (typically green) when the device is turned on.

The device 1 that has just been described allows multiple measurements of force on a patient who is potentially very weak, for example the extension or flexion force of a knee or the abduction of a shoulder or the flexion of an elbow.

For example, in the context of an inflammatory myopathy, inclusion body myositis, it has been possible to validate the quality of the device 1 according to the invention for knee extension by comparing the estimated torque force from the isokinetic/isometric reference device System 3 pro from BIODEX and that estimated from a device according to the invention. The results show an excellent absolute agreement between the two measurement systems.

Of course, the invention is not limited to the examples which have just been described and numerous adjustments can be made to these examples without exceeding the scope of the invention.

For example, in a variant of that which has just been described, the fastening means comprise a suction cup or a magnet or a clamp band or clipping means.

The invention claimed is:

1. A device for measuring a force comprising:
    fastening means configured to fasten the device to a support that is not part of the device;
    a sensor comprising a measuring member arranged to be displaced along a measurement axis, said sensor being arranged to measure a force exerted on the measuring member as a function of the displacement of the measuring member; and
    an outer wall, the sensor being situated inside the outer wall so that the outer wall is equipped with a through hole facing the measuring member along the measurement axis, the measuring member being situated on a face of the sensor so that this face is not in contact with the outer wall,
    the fastening means being attached to the support and arranged so that, during a displacement of the measuring member along the measurement axis, the fastening means exert on the support on which the fastening means are fixed, an average force carried along the measurement axis of the support.

2. The device according to claim 1, wherein the fastening means comprise a vice comprising two jaws, arranged in order to grip the support on which the vice is attached.

3. The device according to claim 1, wherein the fastening means comprise a suction cup or a magnet or a clamp band.

4. The device according to claim 1, wherein the sensor has an accuracy less than or equal to 0.5 N.

5. The device according to claim 1, wherein the sensor has a measuring range of at least 0 N to 900 N.

6. The device according to claim 1, wherein the measuring member is equipped with a screw thread arranged to attach to the measuring member, an external element extending along the measurement axis through the through hole.

7. The device according to claim 1, further comprising at least one electronic board arranged for:
    shaping an electronic signal originating from the sensor into force measurement data, and/or
    supplying the sensor and/or other elements of the device with electricity, and/or
    communicating, to outside the device, force measurement data originating from the sensor, and/or
    storing force measurement data originating from the sensor.

8. The device according to claim 7, wherein the at least one electronic board extends parallel to the measurement axis, under the sensor and under the fastening means.

9. An assembly comprising:
    a device according to claim 7, in which the at least one electronic board is arranged for wireless communication, to outside the device, of force measurement data originating from the sensor; and
    a remote means arranged in order to display the measurement data and/or to process the measurement data, said remote means being connected to said device by a wireless connection.

* * * * *